US005965771A

United States Patent [19]
King et al.

[11] Patent Number: 5,965,771
[45] Date of Patent: *Oct. 12, 1999

[54] REGENERATION OF CARBOXYLIC ACID-LADEN BASIC SORBENTS BY LEACHING WITH A VOLATILE BASE IN AN ORGANIC SOLVENT

[75] Inventors: C. Judson King, Kensington; Scott M. Husson, Berkeley, both of Calif.

[73] Assignee: The Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/943,514

[22] Filed: Oct. 3, 1997

[51] Int. Cl.$^6$ ................................................ C07C 51/42
[52] U.S. Cl. ........................................ 562/580; 562/589
[58] Field of Search .................................. 562/580, 589

[56] References Cited

U.S. PATENT DOCUMENTS

| | | | |
|---|---|---|---|
| 4,275,234 | 6/1981 | Baniel et al. | 562/584 |
| 4,323,702 | 4/1982 | Kawabata | 562/485 |
| 4,405,717 | 9/1983 | Urbas | 435/140 |
| 4,444,881 | 4/1984 | Urbas | 435/139 |
| 4,720,579 | 1/1988 | Kulprathipanja | 562/580 |
| 4,924,027 | 5/1990 | Kulprathipanja | 562/580 |
| 5,132,456 | 7/1992 | King | 562/593 |
| 5,245,078 | 9/1993 | Maeda et al. | 562/580 |
| 5,412,126 | 5/1995 | Poole et al. | 554/185 |

FOREIGN PATENT DOCUMENTS

| | | |
|---|---|---|
| 377430 | 11/1990 | European Pat. Off. |
| 483831 | 6/1992 | European Pat. Off. |
| 907322 | 10/1962 | United Kingdom |
| 1030727 | 5/1966 | United Kingdom |
| 92/16490 | 10/1992 | WIPO |
| 94/19307 | 9/1994 | WIPO |

OTHER PUBLICATIONS

Bartell, F.E., et al., *J. Am. Chem. Soc.*, 45, 1106–1115 (1923).
Busche, R. M. "The Business of Biomass". Biotechnol Progr. 1985, 1, 165–180.
Cullis, C. F., et al., "The Gaseous Oxidation of Tertiary Aliphatic Amines, II.Trimethylamine". Proc. Royal Soc. A 1958, 246, 91–98.
Frierman, M., M.S. Thesis, Dept. of Chemical Engineering, Univ. of California, Berkeley, CA (1983).
Garcia, A.A., et al., *Ind Eng. Chem. Res.*, 28, 204–212 (1989).
Gustafson, R.L., et al., *Ind. Eng. Chem. Fundam.*, 9, 221–229 (1970).
Holten, C. H., Lactic Acid: Properties and Chemistry of Lactic Acid and Derivatives. Verlag Chemie: Copenhagen, 1971.
Jones, P. W., et al., "Formation of Hydrogen from Amine Oxidation and Pyrolysis". Combustion and Flame 1972, 19, 134.

Kertes, A.S., et al. *Biotechnol. Bioeng.*, 28, 269–282 (1986).
Kilduff, J., et al., accepted for publication in Ind. Eng. Chem. Res. (1996).
King, C. J. "Acetic Acid Extraction". In Solvent Extraction Handbook; Lo, T. C.; Baird, M. H. I.; Hanson, C., Eds.; Wiley–Interscience: New York, 1983.
Kuo, Y., et al., "Use of Adsorbents for Recovery of Acetic Acid from Aqueous Solutions. I—Factors Governing Capacity". Separ. & Purif. Methods 1987, 16, 31–64.
Linner, E.R., et al., *J. Phys. Chem.*, 39, 35–67 (1935).
Lipinsky, E. S., et al., "Is Lactic Acid a Commodity Chemical?". Chem. Eng. Progr. 1986, 82 (1), 26–32.
Lockwood, L. B., "Production of Organic Acids by Fermentation". In Microbial Technology; Peppler, H. J.; Perlman, D., Eds.; Academic: New York, 1979; pp. 356–387.
Mitchell, J. A., et al., "The Preparation of Aliphatic Amides". J. Am. Chem. Soc., 1979, 53, 1879–1883.
Pearson, D. E., et al.,"The Variation of Partition Ratios in Mixed Solvents". J. Org. Chem., 1952, 17, 1356–1360.
Poole, L. J., et al., "Regeneration of Amine–Carboxylic Acid Extracts". Report No. LBL–28614; Lawrence Berkeley Laboratory: Berkeley, Calif., 1990.
Poole, L. J. and King, C.J. "Regeneration of Carboxylic Acid–Amine Extracts by Back–Extraction with an Aqueous Solution of a Volatile Amine". Ind. Eng. Chem. Res. 1991 30, 923–929.
Sato, M., et al., "Fermentative Production of Succinic Acid from n–Paraffin by *Candida brumptii* IFO 0731". Agric. Biol. Chem. 1972, 36, 1969–1974.
Tamada, J. A., et al., "Extraction of Carboxylic Acids with Amine Extractants I—Equilibria and Law–of–Mass–Action Modeling". Ind. Eng. Chem. Res. 1990, 29, 1319–1326 (1990).
Tamada, J. A., et al., "Extraction of Carboxylic Acids by Amine Extractants. II—Chemical Interactions and Interpretation of Data". Report No. LBL–25571; Lawrence Berkeley Laboratory: Berkeley, Calif., 1989.
Tamada, J. A., et al., "Extraction of Carboxylic Acids with Amine Extractants. III—Effect of Temperature, Water Co–extraction and Process Considerations". Ind. Eng. Chem. Res. 1990, 29, 1333–1338 (1990).
Tung, L.A., et al., *Ind. Eng. Chem. Res.*, 33, 3217–3223, (1994).
Vickroy, T.B.,*Comprehensive Biotechnology*, vol. 3, Blanch, H.W., S. Drew and D.I.C. Wang, Eds. Pergamon Press, New York, Chap. 38, 761–776 (1985).
Yabannavar, V.M., et al.,*Ann. N.Y. Acad. Sci.*, 506, 523–535 (1987).
Yabannavar, V.M., et al., *Biotechnol. Bioeng.*, 37, 1095–1100 (1991).
Yang, S. T., et al., *Ind. Eng. Chem. Res.*, 30, 1335–1342 (1987).

*Primary Examiner*—Paul J. Killos
*Attorney, Agent, or Firm*—Burns, Doane, Swecker & Mathis, L.L.P.

[57] ABSTRACT

Carboxylic acids are sorbed from aqueous feedstocks onto a solid adsorbent. The acids are freed from the sorbent phase by treating it with an organic solution of alkylamine thus forming an alkylamine/carboxylic acid complex which is decomposed with improved efficiency to the desired carboxylic acid and the alkylamine. Carbon dioxide addition can be used to improve the adsorption or the carboxylic acids by the solid phase sorbent.

34 Claims, 6 Drawing Sheets

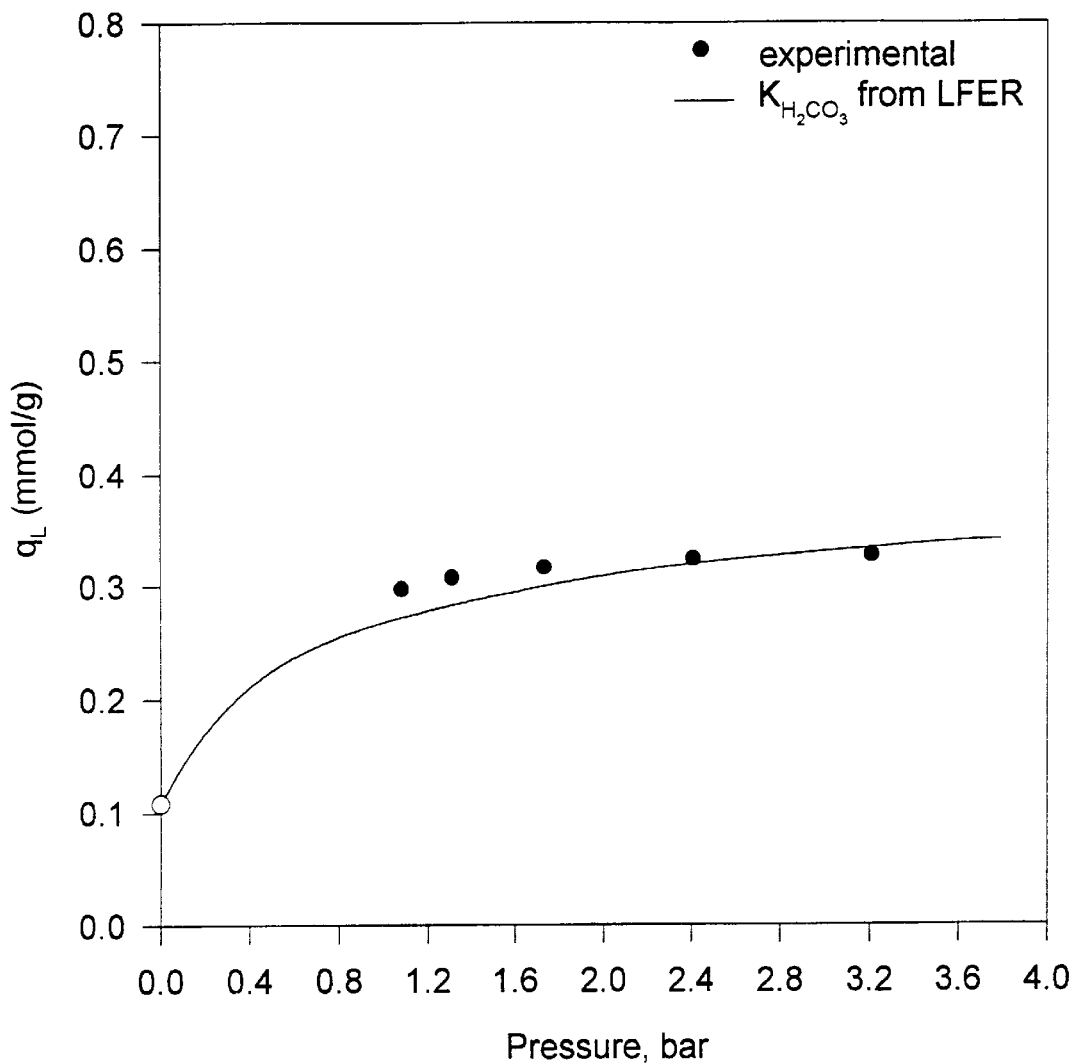
FIG. 7. Lactic acid uptake onto Dowex MWA-1 from a 0.05 M sodium lactate solution in equilibrium with a vapor comprised of primarily $CO_2$. The open circle represents uptake in the absence of $CO_2$.

REGENERATION OF CARBOXYLIC ACID-LADEN BASIC SORBENTS BY LEACHING WITH A VOLATILE BASE IN AN ORGANIC SOLVENT

ORIGIN OF THE INVENTION

This invention was made in the performance of work funded by the "Biochemical and Chemical Technology Research" (BCTR) program of the United States Department of Energy under Contract No. DE-AC03-76SF00098. The United States Government has rights to this invention.

FIELD OF THE INVENTION

The invention relates to chemical engineering. Specifically it relates to sorption processes for removing carboxylic acids from aqueous streams. More particularly it relates to improvements in recovering sorbed carboxylic acids from solid phase sorbents.

BACKGROUND OF THE INVENTION

Carboxylic acids are important chemicals of commerce. They appear as desired or contaminating constituents of a wide range of aqueous process streams. There are many instances where it is important to remove and/or recover carboxylic acids from aqueous solutions. Examples include product recovery in the manufacture of chemicals from biomass by fermentation and both product recovery and processing of aqueous wastes in the petrochemical, chemical, pulp and paper industries. There are also applications in other industries based upon biological materials, such as corn wet milling and processing of grains and food oils. Acids commonly of interest are acetic, formic, succinic, adipic, fumaric, maleic, lactic, malic and citric acids. There is strong industrial interest in lactic acid as a precursor to biodegradable plastics.

Present separation techniques for removal and recovery of carboxylic acids are energy-intensive and therefore expensive. Some, such as the classical method for recovery of citric and lactic acids by precipitation of calcium salts, also consume large volumes of chemicals (e.g., sulfuric acid and lime) and create large volumes of waste (e.g., calcium sulfate). Recovery technology using reversible chemical complexation with agents such as polymeric sorbents with amine functionalities can reduce energy consumption substantially. If an appropriate method of regeneration, allowing recovery and reuse of all agents, is utilized, such processes can also avoid production of waste salts and net consumption of chemical agents.

Previous researchers (Kertes and King, 1986; Tamada, et al., 1990; Yabannavar and Wang, 1987, 1991; Yang, et al., 1987; Garcia and King, 1989) have shown that extraction and adsorption by reversible chemical complexation are effective for recovery of carboxylic acids from dilute aqueous solutions. Amine-based extractants and adsorbents sustain uptake capacity for carboxylic acids from solutions at pH above the $pK_{a1}$ of the acid, where the acid exists mostly as the carboxylate anion. However, these strongly basic complexing agents require correspondingly strong methods for regeneration (Tung and King, 1992, 1994). In this connection, it has been proposed in the art to add carbon dioxide to the extraction zone in an extraction process to provide carbonic acid to push the acid equilibrium in the direction of the free acid form, to enhance acid recovery (Baniel, Eyal, et al., 1996).

One approach to regenerating strongly basic extractants and adsorbents is leaching with an aqueous solution of a strong base (e.g., NaOH or $Ca(OH)_2$) to form the carboxylate salt. A strong acid (e.g., $H_2SO_4$) must then be added to liberate the carboxylic acid product. This approach necessarily consumes chemicals and produces a waste salt by-product.

A second approach involves leaching with an aqueous solution of a volatile base, such as trimethylamine (TMA) (Poole and King, 1991, 1995). The resulting trimethylammonium carboxylate can be decomposed thermally, yielding acid product and recovering the TMA, making it available to recycle. For slightly soluble acids, such as succinic and fumaric, partial evaporation of the aqueous trimethylammonium carboxylate solution results in precipitation of the acid product (Poole and King, 1991). However, for lactic acid, which is highly soluble in water, the thermal decomposition of trimethylammonium lactate is incomplete (Poole and King, 1991), leaving about 0.6 mols TMA/mol lactic acid under the conditions used.

Ion exchange and adsorption have also been employed in carboxylic acid recovery schemes. U.S. Pat. No. 4,720,579 to Kulprathipanja discloses the use of styrene-divinylbenzene resins to adsorb citric acid with regeneration by water or by a mixture of acetone and water. Similarly, U.S. Pat. No. 4,323,702 to Kawabata discloses the use of adsorbents containing pyridyl functional groups combined with regeneration by leaching with an organic solvent such as an alcohol or a ketone. U.S. Pat. No. 4,924,027 to Kulprathipanja and Strong discloses adsorption of citric acid by adsorbents containing tertiary amine or pyridyl functionalities (including Bio-Rad AG3-X4A and AG4-X4), with regeneration using an aqueous solution of sodium, potassium or ammonium hydroxide, yielding the respective sodium, potassium or ammonium citrate. Treatment of these citrates with a strong acid would yield the free citric acid form, but again consumes an acid and a base and produces a waste salt stream. In each of these solutions the citric acid is adsorbed from an aqueous solution below the $pK_{a1}$ of citric acid.

As can be seen from this description of background, various methods used heretofore to recover carboxylic acids have presented limitations and thus offer opportunities for improvement. It is accordingly a general objective of the invention to provide an efficient process for the recovery of carboxylic acids from aqueous solutions which neither consumes large amounts of chemicals nor generates waste chemical streams.

REFERENCES

The following references relate to the general subject matter of the present invention:

Baniel, A. M.; Blumberg, R.; Hajdu, K. "Recovery of Acids from Aqueous Solutions". U.S. Pat. No. 4,275,234, Jun. 23, 1981.

Baniel, A. M.; Eyal, A. M.; Mizrahi, J.; Hazan, B.; Fisher, R.; Kolstad, J. J.; Stewart, B. F. "Lactic Acid Production, Separation and/or Recovery Process". U.S. Pat. No. 5,510,526, Apr. 23, 1996.

Bartell, F. E.; Miller, E. J. "Adsorption by Activated Sugar Charcoal". *J. Am. Chem. Soc.* 1923, 45, 1106–1115.

Buschc, R. M. "The Business of Biomass". *Biotechnol. Progr.* 1985, 1, 165–180.

Cullis, C. F.; Waddington, D. J. "The Gaseous Oxidation of Tertiary Aliphatic Amines, II. Trimethylamine". *Proc. Royal Soc. A.* 1958, 246, 91–98.

Frierman, M. "The Use of Solid Adsorbents for the Recovery of Acetic Acid from Aqueous Solutions". M. S. Thesis, University of California at Berkeley, 1983.

Garcia, A. A.; King, C. J. "The Use of Basic Polymeric Sorbents for the Recovery of Acetic Acid from Dilute Aqueous Solution". *Ind. Eng. Chem. Res.* 1989, 28, 204–212.

Gustafson, R. L.; Fillius, H. F.; Kunin, R. "Basicities of Weak Base Ion Exchange Resins". *Ind. Eng. Chem. Fundam.* 1970, 9, 221–229.

Holten, C. H. *Lactic Acid: Properties and Chemistry of Lactic Acid and Derivatives;* Verlag Chemie: Copenhagen, 1971.

Jones, P. W.; Gesser, H. D. "Formation of Hydrogen from Amine Oxidation and Pyrolysis". *Combustion and Flame* 1972, 19, 134.

Kawabata, N.; Yasuda, S.; Yamazaki, T. "Process for Recovering a Carboxylic Acid". U.S. Pat. No. 4,323,702, Apr. 6, 1982.

Kertes, A. S.; King, C. J. "Extraction Chemistry of Fermentation Product Carboxylic Acids". *Biotechnol. Bioeng.* 1986, 28, 269–282.

Kilduff, J.; King C. J. "Effect of Carbon Adsorbent Surface Properties on the Uptake and Solvent Regeneration of Phenol". *Ind. Eng. Chem. Res.,* in press.

King, C. J. "Acetic Acid Extraction". In *Solvent Extraction Handbook;* Lo, T. C.; Baird M. H. I.; Hanson, C., Eds.; Wiley-Interscience: New York, 1983.

Kulprathipanja, S. "Separation of Citric Acid from Fermentation Broth with a Neutral Polymeric Adsorbent". U.S. Pat. No. 4,720,579, Jan. 19, 1988.

Kulprathipanja, S.; Strong S. A. "Separation of Salts of Citric Acid from Fermentation Broth with a Weakly Basic Anionic Exchange Resin Adsorbent". U.S. Pat. No. 4,924,027, May 8, 1990.

Kuo, Y.; Munson, C. L.; Rixey, W. G.; Garcia, A. A.; Frierman, M.; King, C. J. "Use of Adsorbents for Recovery of Acetic Acid from Aqueous Solutions. I. Factors Governing Capacity". *Separ. Purif. Methods* 1987, 16, 31–64.

Linner, E. R.; Gortner, R. A. "Interfacial Energy and the Molecular Structure of Organic Compounds. III. The Effect of Organic Structure on Adsorbability". *J. Phys. Chem.* 1935, 39, 35–67.

Lipinsky, E. S.; Sinclair, R. G. "Is Lactic Acid a Commodity Chemical?". *Chem. Eng. Progr.* 1986, 82, 26–32.

Lockwood, L. B. "Production of Organic Acids by Fermentation". In *Microbial Technology,* Peppler, H. J.; Perlman, D., Eds.; Academic: New York, 1979; pp 356–387.

Mitchell, J. A.; Reid, E. E. "The Preparation of Aliphatic Amides". *J Am. Chem. Soc.* 1931, 53, 1879–1883.

Pearson, D. E.; Levine, M. "The Variation of Partition Ratios in Mixed Solvents". *J Org. Chem.* 1952, 17, 1356–1360.

Poole, L. J.; King, C. J. "Carboxylic Acid Sorption Regeneration Process". U.S. Pat. No. 5,412,126, May 2, 1995.

Poole, L. J.; King, C. J. "Regeneration of Amine-Carboxylic Acid Extracts". Report No. LBL-28614; Lawrence Berkeley Laboratory: Berkeley, Calif., 1990.

Poole, L. J.; King, C. J. "Regeneration of Carboxylic Acid-Amine Extracts by Back-Extraction with an Aqueous Solution of a Volatile Amine". *Ind. Eng. Chem. Res.* 1991, 30, 923–929.

Sato, M.; Nakahara, T.; Yamada, K. "Fermentative Production of Succinic Acid from n-Paraffin by Candida brumptii IFO 0731". *Agric. Biol. Chem.* 1972, 36, 1969–1974.

Tamada, J. A.; Kertes, A. S.; King, C. J. "Extraction of Carboxylic Acids with Amine Extractants. I. Equilibria and Law-of-Mass-Action Modeling". *Ind. Eng. Chem. Res.* 1990, 29, 1319–1326.

Tamada, J. A.; King, C. J. "Extraction of Carboxylic Acids with Amine Extractants. II. Chemical Interactions and Interpretation of Data". *Ind. Eng. Chem. Res.* 1990, 29, 1327–1333.

Tamada, J. A.; King, C. J. "Extraction of Carboxylic Acids with Amine Extractants. III. Effect of Temperature, Water Co-Extraction and Process Considerations". *Ind. Eng. Chem. Res.* 1990, 29, 1333–1338.

Tung, L. A.; King, C. J. "Sorption and Extraction of Lactic and Succinic Acids at pH>$pK_{a1}$. 1. Factors Governing Equilibria". *Ind. Eng. Chem. Res.* 1994, 33, 3217–3223.

Tung, L. A.; King, C. J. "Sorption of Carboxylic Acid from Carboxylic Salt Solutions at pHs Close to or Above the $pK_a$ of the Acid, with Regeneration with an Aqueous Solution of Ammonia or Low-Molecular-Weight Alkylamine". U.S. Pat. No. 5,132,456, Jul. 21, 1992.

Urbas, B. "Recovery of Acetic Acid from a Fermentation Broth". U.S. Pat. No. 4,405,717, Sep. 20, 1983.

Urbas, B. "Recovery of Organic Acids from a Fermentation Broth". U.S. Pat. No. 4,444,881, Apr. 24, 1984.

Vickroy, T. B. "Lactic Acid". In *Comprehensive Biotechnology;* Blanch, H. W.; Drew, S.; Wang, D. I. C., Eds.; Pergamon: New York, 1985; Vol 3, Chapter 38.

Yabannavar, V. M.; Wang, D. I. C. "Bioreactor System with Solvent Extraction for Organic Acid Production". *Ann. NY Acad. Sci.* 1987, 506, 523–535.

Yabannavar, V. M.; Wang, D. I. C. "Extractive Fermentation for Lactic Acid Production". *Biotechnol. Bioeng.* 1991, 37, 1095–1100.

Yang, S. T.; White, S. A.; Hsu, S. T. "Extraction of Carboxylic Acids with Tertiary and Quarternary Amines: Effect of pH". *Ind. Eng. Chem. Res.* 1987, 30, 1335–1342.

SUMMARY OF THE INVENTION

We have now found an improvement in the process for carboxylic acid recovery from solid sorbents in which the acid is converted into an alkylammonium carboxylate which is then thermally decomposed. We have now discovered that the likely cause of the incomplete thermal decomposition of alkylammonium carboxylates recovered from the solid sorbent is the aqueous environment in which the decomposition is carried out in the prior art. This aqueous environment promotes ionization of the alkylammonium carboxylate salt, thereby suppressing the volatility of the alkylamine and stabilizing the alkylammonium carboxylate salt in the liquid phase. We have found that an effective alternative approach is to employ the alkylamine in an organic solvent, instead of in water. This organic solution of the alkylamine is used to solubilize sorbed carboxylic acid from the solid sorbent as an alkylamine/carboxylic acid complex. The resulting organic solution is heated and concentrated, thereby decomposing the alkylamine/carboxylic acid complex fully.

In the organic solvent, the basicity of the amine is reflected primarily through Lewis acid/Lewis base (e.g., hydrogen bonding) interactions, rather than through protonation (ionization) as is the case for the alkylamine carboxylate in an aqueous solution. Suppression of ionization in the organic solution promotes thermal decomposition of the alkylamine/carboxylic acid complex.

After removal of the alkylamine through thermal decomposition and vaporization, product carboxylic acid can be recovered by evaporative crystallization from the organic solvent or by other means. Alternatively, if an aqueous concentrate is the desired product, the carboxylic acid can be transferred from the organic solvent to water in a dual-feed distillation, provided that the organic solvent is sufficiently miscible with water at distillation temperature.

The concept can be exemplified in terms of lactic acid and trimethylamine; however, it is extensible to other carboxylic acids, and potentially to other volatile bases, (e.g., other low-molecular-weight amines). It can be exemplified in terms of a simple adsorption/recovery scheme. It can also be employed in conjunction with the addition of carbon dioxide and other materials known to improve the recovery of acids from solutions.

Our discovery can be embodied as an improved overall process for isolating and recovering carboxylic acids from carboxylic acid-containing aqueous streams. It can also be viewed as an improved method for recovering sorbed carboxylic acids from solid phase acid sorbents and thus regenerating the solid sorbents.

Viewed as an overall process, the carboxylic acids are first removed from the aqueous stream by a solid phase adsorption technique. The sorbed carboxylic acid is then recovered by contacting the sorbent phase with an organic solution of an alkylamine. This "back-extracts" or solubilizes the carboxylic acid into the organic extraction phase as an alkylamine/carboxylic acid complex. When this organic solution is heated, the alkylamine/carboxylic acid complex decomposes completely to yield the carboxylic acid which can then be recovered. The alkylamine is also regenerated and can be recycled. Thus, a process is achieved which consumes no substantial amount of chemicals and generates no substantial amount of waste by-product.

In another aspect, this invention provides a process for regenerating carboxylic acid-laden solid sorbent phases. This regeneration process involves contacting the acid-laden solid with an organic solution of alkylamine. In this way, the sorbed carboxylic acid is removed, and an organic solution of an alkylamine/carboxylic acid complex is formed. The alkylamine/carboxylic acid complex is then completely and efficiently thermally decomposed to give the corresponding acid which is recovered and the corresponding amine which is recycled.

We have also discovered that processes in which carboxylic acids are first removed from the aqueous stream by a solid phase adsorption technique can be improved by carrying out the adsorption in the presence of a positive pressure of added carbon dioxide under conditions whereby carboxylic acid is sorbed from the feed stream to the solid phase acid sorbent and carbon dioxide is converted into carbonate and/or bicarbonate, thereby forming an acid-depleted, carbonate and/or bicarbonate-containing aqueous feed stream and an acid-enriched solid phase acid sorbent. Then the acid-depleted, carbonate and/or bicarbonate-containing aqueous feed stream is separated from the acid-enriched solid phase acid sorbent. The acid-enriched solid phase acid sorbent can then be treated, such as by contact with a desorbing solution comprising an alkylamine in an organic solvent, thereby solubilizing the carboxylic acid from the sorbing phase into the desorbing solution as an alkylamine/carboxylic acid complex, and forming a carboxylic acid-lean solid phase acid sorbent. These materials can be treated as described herein. Of course, other methods for recovering the sorbed acid from the solid phase sorbent can be applied, if desired.

In this aspect of the invention it may also be desired to treat the acid-depleted, carbonate and/or bicarbonate-containing aqueous feed stream to convert carbonate and/or bicarbonate to carbon dioxide for recycle to the adsorption zone.

DETAILED DESCRIPTION OF THE INVENTION

BRIEF DESCRIPTION OF THE DRAWINGS

In this description of the invention, reference will be made to the accompanying drawings, in which:

FIG. 7 is a graph illustrating the improvement in carboxylic acid uptake onto a solid phase adsorbent when carbon dioxide is present in the adsorption zone.

DESCRIPTION OF PREFERRED EMBODIMENTS

This section is arranged as follows:

First, two representative embodiments of the overall PROCESS of the invention are described with reference to FIG. 1 and FIG. 6; next, typical AMINES which may be used in the process are described together with the ORGANIC LIQUIDS in which they are dissolved; then, the various acid-sorbing SOLID PHASES are described; followed by, a description of typical ACIDS which may be recovered by the process; and finally, experimental details verifying the efficiency of the process are given in the form of EXAMPLES.

The Process

The present invention regenerates acid-laden carboxylic acid-sorbing solid sorbents by solubilizing the sorbed carboxylic acids directly with an organic solvent-based solution of alkylamine to give organic solutions of alkylamine/carboxylic acids. These complexes are then decomposed to yield the alkylamine and the carboxylic acid which is recovered. This regeneration process is illustrated as part of an overall process in FIG. 1. Other process configurations may be used as well to implement the concept. Examples include the rotating-valve "Sorbex" process of UOP, Inc., and various multi-bed processes.

Figure 1:
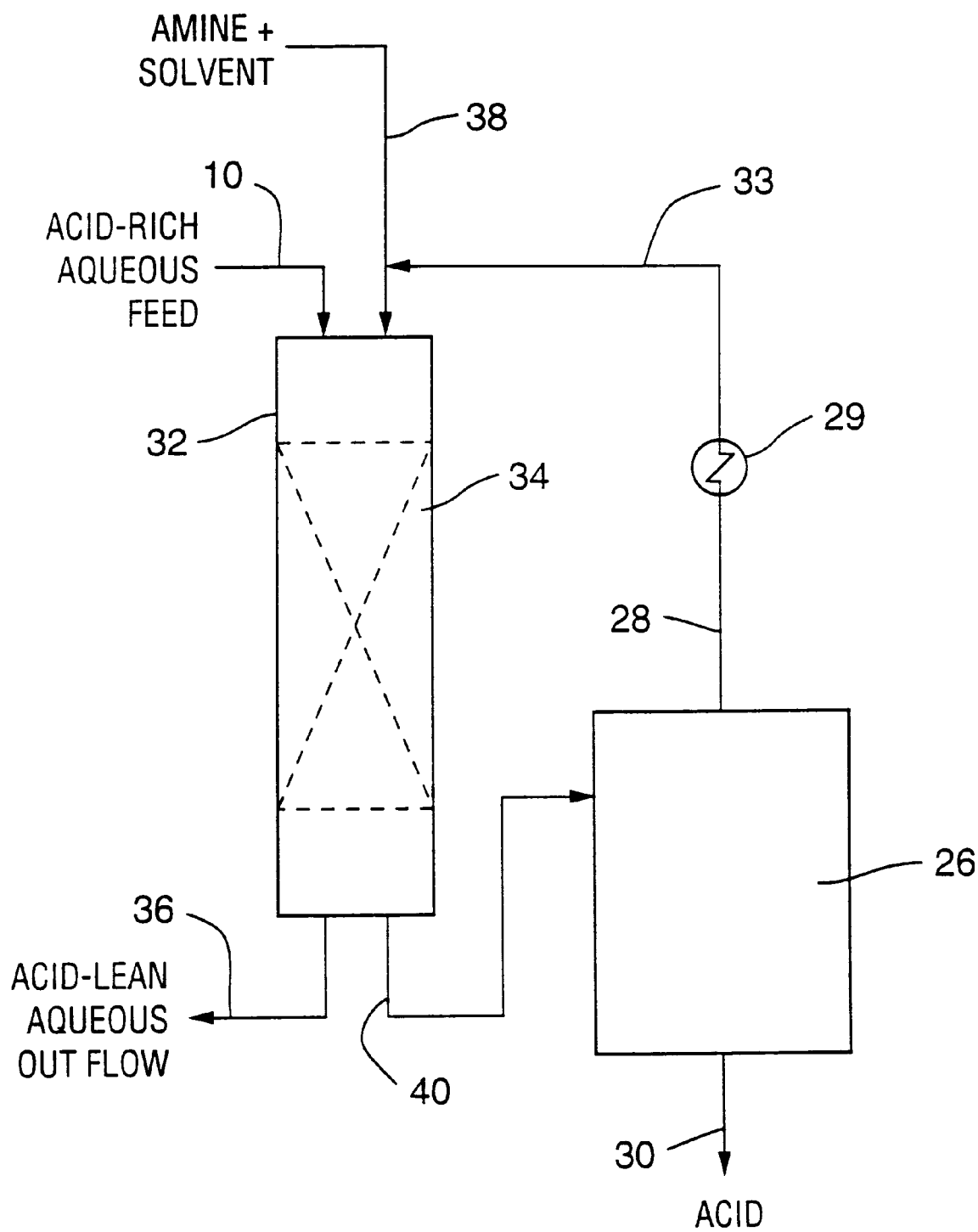
FIG. 1 is a schematic flow diagram illustrating the process of the invention embodied as a solid phase adsorption process.

In FIG. 1 an aqueous feed stream which comprises a water-based solution having from a few parts per million to about saturation of carboxylic acid is fed through line 10 to contactor 32. Contactor 32 contains a bed of solid phase acid sorbent 34. This solid or gel sorbent may be a relatively basic material such as an amine-containing resin or the like so as to adsorb selectively the carboxylic acid groups out of the acid-rich aqueous feed. The sorbent thus produces an acid-lean aqueous outflow which is recovered from the acid-sorbing solid phase and taken out of contactor 32 via line 36. The outflow in line 36 can be suitably monitored until a breakthrough in carboxylic acid level is noted in the outflow, indicating that the solid sorbent 34 has removed its capacity of carboxylic acid. At this point, feed line 10 is closed via means not shown and aqueous outflow line 36 is also closed. An organic solution of alkylamine is then fed to contactor 32 via line 38. The alkylamine is most commonly an alkylamine of low molecular weight. The alkylamine and the solid sorbing phase are matched so that the amine is a strong enough base to regenerate the solid sorbent. This causes the amine to react with the sorbed carboxylic acid and form an alkylamine/carboxylic acid complex, which is soluble in the organic solvent phase and thus carried out of contactor 32 via line 40. This has the effect of regenerating the acid-sorbing phase so that it may be reused.

The solution of alkylamine/carboxylic acid complex in organic solvent is then passed to decomposing zone 26. There, heat (and optionally reduced pressure) is applied so as to evaporate the solvent to the extent that may be necessary and to decompose the alkylamine/carboxylic acid complex into the corresponding alkylamine and carboxylic acid. A particular advantage of the present invention is that this decomposition can be carried out to completion with minimal loss of amine or acid. In prior water-based systems, this decomposition could not be carried to completion for highly water-soluble carboxylic acids such as lactic acid. If, as is usually the case, the alkylamine is more volatile than the acid, the alkylamine can be taken off overhead, typically in combination with the organic solvent. The mixture of solvent and alkylamine can be taken overhead via line 28, condensed in condenser 29 and recycled to line 38 via line 33.

The acid which is freed by this decomposition and amine/solvent removal is taken off of decomposer 26 via line 30 either as crystals or as a liquid acid or as a highly saturated solution, depending upon the tendency of the carboxylic acid to crystallize. The carboxylic acid can be simply recovered from this product and subjected to purification steps if desired.

Although the exact conditions employed will depend in part upon the equipment employed and in part upon the nature of the aqueous feedstock, it is generally preferred to use a quantity of solid sorbent and a contact time adequate to remove a substantial fraction of the desired carboxylic acid from the aqueous feed. This generally means that the number of equivalents of acid-sorbing groups such as amines or the like present in the solid phase should exceed or at least equal the number of equivalents of acid present in the aqueous feed passing through the bed during the cycle period. Typical contact times range from about a minute to as much as an hour or more. This contacting can be carried out at any desired temperature, with ambient temperature offering the most advantageous cost.

The desorbing of the acid off of the solid sorbent phase involves contacting the solid phase with the organic solution of alkylamine. This contacting employs residence times that are typically selected from about one minute to about three hours, although longer times may be used if convenient. It is generally desirable to use a relatively concentrated solution of alkylamine in this contacting. For this purpose, the alkylamine can be dissolved in the organic solution under pressure.

Figure 3:
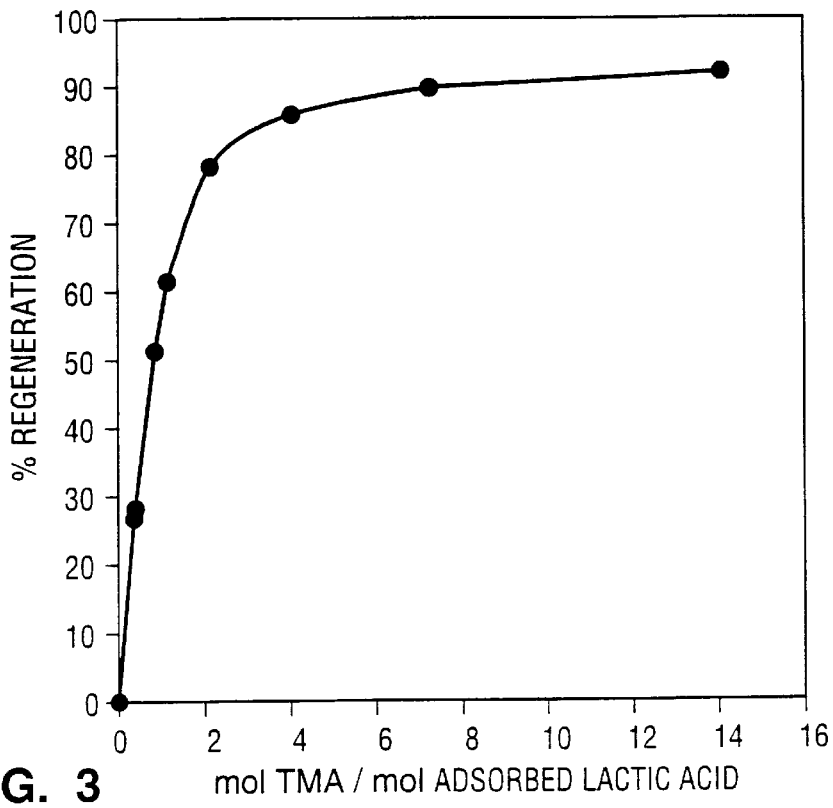
FIG. 3 is a graph illustrating the regeneration of lactic-acid-laden Dowex MWA-1 by leaching with an organic solution of trimethylamine at 25 degrees centigrade.

As demonstrated in the Examples and illustrated in FIG. 3, the completeness of desorption depends at least in part upon the amount of alkylamine employed during the regeneration cycle. At least one equivalent of amine should be employed for each equivalent of acid being desorbed. Substantially complete desorption occurs whenever the amount of alkylamine in equivalents in the organic phase is greater than the number of equivalents of carboxylic acid being recovered from the solid sorbent. Typically, very complete desorption occurs with from about 1.0 to 25 equivalents of amine based on acid and especially from about 2 to 12 equivalents of amine based on acid. A 90% maximum regeneration reflects the presence of about 10% quaternary ammonium groups on the resin employed in the experiments.

The decomposition stage 26 serves to decompose the amine/carboxylic acid complex into the free alkylamine and the free acid. As the decomposition progresses, either the free acid or the free amine, or both, are removed, driving the decomposition forward and permitting a more complete decomposition of the complex and recovery of acid. In the embodiment shown in FIG. 1, the amine is taken overhead and removed, and the acid is removed as well, as a bottoms product.

The decomposition step is carried out under relatively mild conditions such as a temperature of from about 20° C. to about 200° C. and particularly 30° C. to 175° C., an average residence time of from about 1 minute to 3 hours and especially 2 minutes to 2 hours, and a pressure from about 50 torr (vacuum) to about 2 atmospheres. An upper limit may be placed upon the temperature by the need to avoid decomposition or discolorization of the carboxylic acid.

In determining the extent to which the complex is decomposed, and the conditions used to effect these processes, one must bear in mind the fact that the free carboxylic acids can react with non-tertiary alkylamines (i.e., monoalkylamines or dialkylamines) to give amides. If a non-tertiary alkylamine is present and is exposed to the carboxylic acid for prolonged periods at elevated temperature, a lower yield may result.

Ultimately, the acid should be obtained as free of residual alkylamine/carboxylic acid complex and contaminating alkylamine as possible. This can be facilitated by various washings, crystallizings and the like as needed. Representative levels of complex decomposition range from about 25% up to essentially 100%, and commonly are in the 90–100% range.

It is generally preferred to carry out the steps of this process, especially the decomposition, in an oxygen-free or reduced-oxygen environment such as an inert gas blanket to minimize oxidation of the amine.

The acid recovered via line 30 in this process is typically present as a slurry of solid in organic liquid or as a concentrated/saturated/supersaturated solution in the liquid. This stream can be further processed to purify the acid-containing material, to decolorize it, further remove amine from it and otherwise isolate it. These steps are optional.

It will be appreciated by those of skill in the art that it is important from a cost point of view to minimize the loss of the organic solvent and the amine regenerant while practicing this invention. To this end, it may be of advantage to have rinse steps in the process. For example, after the acid has been removed from the solid sorbent by the use of the organic solution of amine, there will be substantial residual amounts of the organic solvent and alkylamine associated with the solid sorbent. If the regenerated bed of solid sorbent is placed back in service and contacted with a fresh charge of acid-containing aqueous feedstock, this residual solvent and amine will be lost. A rinse step, either a water rinse step or an organic solvent followed by water rinse sequence would allow the residual solvent to be removed in a stream from which it could be removed by distillation or the like.

Similarly, the processing advantages provided by the present invention are maximized if the water content is minimized in the amine/carboxylic acid-containing organic solution during decomposition. It is preferred if the water content of the decomposition feed is less than 3% by weight, based on the overall feed and more preferred if this value is less than 1%. Thus, it may be of advantage to rinse the solid sorbent with a solvent to remove residual water prior to contacting the solid sorbent with the organic solution of alkylamine. This rinse phase can be treated such as by distillation to separate out water and provide the solvent in dry form for recycle. A second function of the rinse step is to remove any non-selectively sorbed compounds present in the aqueous feed (e.g., sugars) that could otherwise interfere with acid purification.

Figure 6:
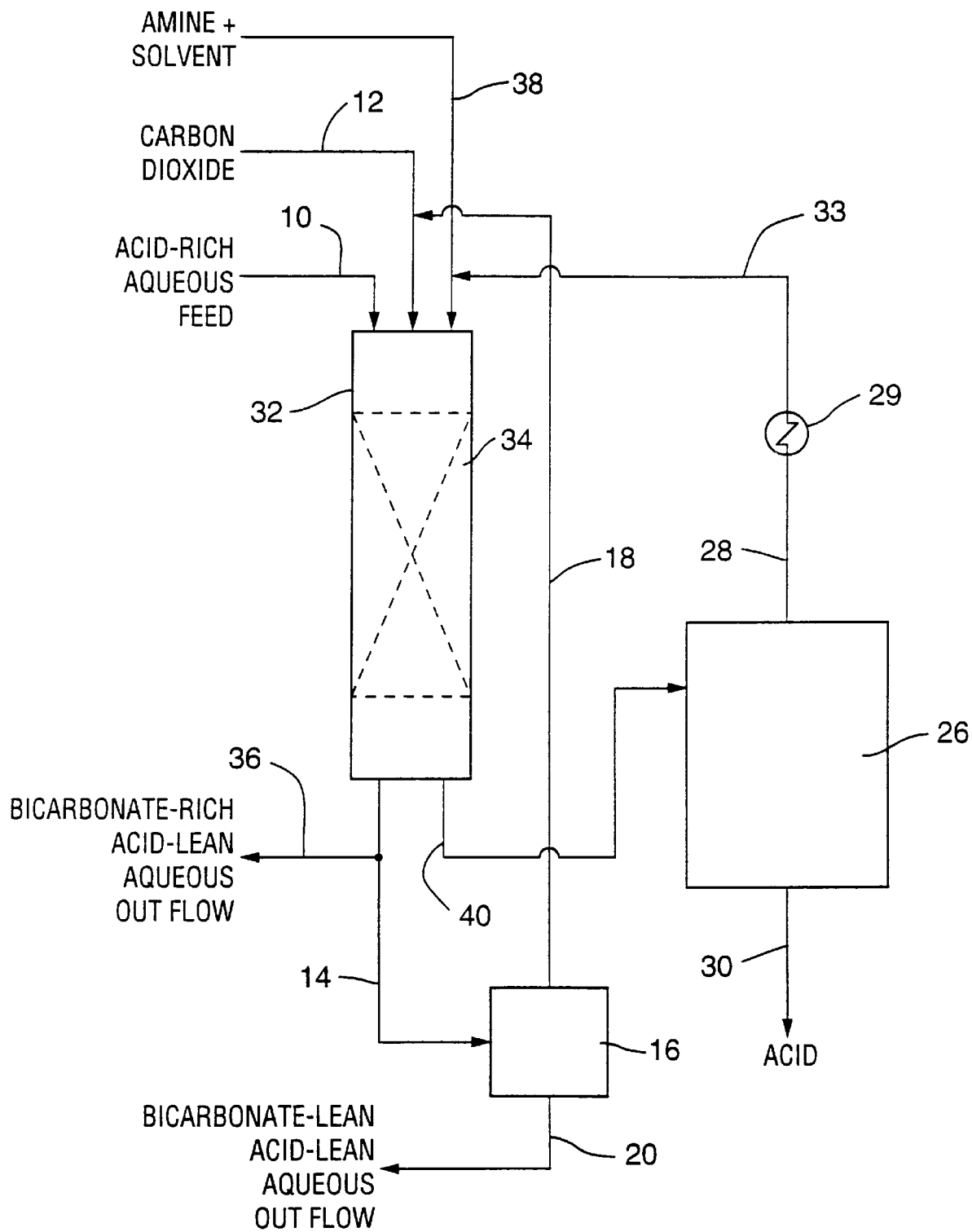
FIG. 6 is a schematic flow diagram illustrating the process of the invention embodied as a solid phase adsorption process carried out in the presence of added carbon dioxide.

Turning to FIG. 6, the present invention is shown there employed in conjunction with the addition of carbon dioxide to the adsorption zone. In this embodiment, the general operating parameters set forth in FIG. 1 are followed. A positive presence of carbon dioxide gas is added to contactor 32 via line 12. As pointed out by Baniel, Eyal, et al., partial pressures of carbon dioxide in the range of 50 psig or greater enhances the recovery of acid from the acid-rich aqueous feed provided via line 10. We have found for adsorption that under appropriate conditions, pressures lower than 50 psig are usable such as pressures of from about 10 or 15 psig. Higher pressures such as up to 200 psig or greater could be used but will result in the need for heavier duty equipment. Pressures of from about 15 psig to about 150 psig are preferred. The aqueous outflow removed from contactor 32 via line 36 includes carbonate and/or bicarbonate as well as dissolved carbon dioxide. This stream can be removed or, if desired, passed via line 14 to carbon dioxide recovery zone 16. In zone 16, the aqueous outflow stream can be depressured and/or to release dissolved carbon dioxide to release additional carbon dioxide. This carbon dioxide is recycled via line 18 to contactor 32 and the carbon-dioxide depleted aqueous phase removed via line 20. The organic solution of acid is removed via line 40 and processed as described in FIG. 1.

The Organic Solution of Alkylamine

An important element of the present invention is the use of an organic solution of alkylamine as the desorbent material. This alkylamine material is also sometimes referred to herein as a low molecular weight amine or the like.

The alkylamine can be a mono-, di- or trialkylamine. It is selected to have substantial solubility in the organic solvent phase, that is a solubility in the organic back-extraction solvent, of at least about 1% by weight and preferably at least about 2% by weight.

Of these materials, the trialkylamines offer an advantage of not being capable of forming amides with the recovered acids. The mono- and dialkyl materials can enter into this irreversible side reaction if prolonged contact with the acid at elevated temperatures occurs.

Another factor to be taken into account is that the amine must have sufficiently high basicity to effect regeneration.

Another factor to be taken into account in selecting an amine is its boiling point relative to the boiling point of the organic solvent and the free acid. If volatilization of the amine is to be used as the mechanism to separate the amine from the acid, a difference in boiling point between them is necessary.

Still another factor to be taken into account in selection of an amine is the susceptibility of the amine to thermal decomposition and/or oxidation.

Of the trialkylamine materials, preference is given to trimethylamine (TMA) for a number of reasons. First, it is the most common and least expensive of these materials. Also, it has a high solubility in organic solvents and thus allows a concentrated desorbent to be formed. Third, it is the most volatile of the trialkylamines (2.9° C. b.p.) and thus, upon decomposition of the trimethylamine/carboxylic acid complexes, can be removed overhead by distillation with the least amount of heating of the organic regenerant solution. Other trialkylamines containing up to about 6 or even 8 total carbon atoms—for example dimethylethylamine, methyldiethylamine, triethylamine, dimethyl-n-propylamine, dimethyl-i-propylamine, methyldi-n-propylamine, dimethylbutylamine and the like—may be used. Monoalkylamines of up to about 6 carbons such as methylamine, ethylamine, propylamine, butylamine, pentylamine and hexylamine and dialkylamines of up to about 8 total carbons such as dimethylamine, diethylamine, dibutylamine and the like can also be used as long as their potential for side reactions is kept in mind. Mixtures of amines can be used.

The alkylamine in organic solution should supply a sufficiently large driving force for regeneration of the solid sorbent. In addition to its ability to effectively compete with the basic sites of the sorbent for the acid, the base must be removable from the sorbent under conditions which will not degrade the sorbent. Based on these criteria, TMA is the preferred regenerant amine for many applications.

In accord with this invention, these alkylamines are employed as an organic solution. The solvent for this solution is selected to satisfy the following criteria. The solvent should (1) not react with the acid, the amine, or the sorbent, (2) be easily removed from the solid sorbent under conditions which do not degrade the sorbent, (3) be sufficiently different in volatility to be easily removed from the acid, (4) have a high solubility for the amine, and (5) have a boiling point high enough for the cracking reaction to occur at a reasonable rate and low enough to prevent side reactions (e.g., production of lactoyllactic acid). It is also preferable if the solvent solvates the acid more effectively than the acid-amine complex. Using these criteria, suitable solvents can be selected from ketones, ethers, esters and aldehydes. Aldehydes can be reactive in a number of ways which may limit their use. Alcohols can also be used but do pose the problem that they can form esters with the desired acids.

In terms of boiling points, generally materials having boiling points in the range of from about 40 to 175° C. are suitable with materials having a boiling point in the range of about 50 to about 160° C. being preferred. In terms of molecular size, typically these solvents have from about 3 to about 8 carbons and preferably 4 to 8 carbons and most commonly a single ketone, aldehyde, ether or ester functionality. Table 1 lists representative solvents which may be used.

TABLE 1

Suitable Solvents

Non-cyclic Aldehydes

Propanal
Isobutyraldehyde
Butanal
2-methylbutyraldehyde
3-methylbutyraldehyde
Pentanal
2-ethylbutyraldehyde
2-ethylpentyraldehyde
3-methylpentylraldehyde
4-methylpentylraldehyde
Hexanal
2-ethyl-3-methylbutyraldehyde
2,3-dimethylpentyraldehyde
2,4-dimethylpentyraldehyde
3,4-dimethylpentyraldehyde
2-ethylpentyraldehyde
3-ethylpentyraldehyde
2-methylhexyraldehyde
3-methylhexyraldehyde
4-methylhexyraldehyde

TABLE 1-continued

Suitable Solvents 5-methylhexyraldehyde
Heptanal
Cyclic Aldehydes

Cyclopropaldehyde
Cyclobutylaldehyde
Furfural
Non-cyclic Ketones

Acetone
Methyl ethyl Ketone
Methyl isopropyl ketone
2-Pentanone
3-Pentanone
Pinacolone
Ethyl isopropyl ketone
Methyl isobutyl ketone
Methyl sec-butyl ketone
Diisopropyl ketonoe
2-Hexanone
3-methyl-2-hexanone
4-methyl-2-hexanone
5-methyl-2-hexanone
4-Heptanone
3,3-dimethyl-2-pentanone
3,4-dimethyl-2-pentanone
4-methyl-3-hexanone
5-methyl-3-hexanone
2,2-dimethyl-3-pentanone
2-Heptanone
3-Heptanone
Cyclic Ketones Cyclopropanone
Methylcyclopropanone
Cyclobutanone
Methyl cyclopropyl ketone
Ethylcyclopropanone
Dimethylcyclopropanone
Methylcyclobutanone
Cyclopentanone
Methyl cyclobutyl ketone
Ethyl methyl cyclopropanone
Propylcyclopropanone
2-ethyl cyclobutanone
3-ethyl cyclobutanone
1,1-dimethylcyclobutanone
1,2-dimethylcyclobutanone
2-methyl cyclopentanone
3-methyl cyclopentanone
Cyclohexanone
Non-cyclic Ethers Isopropyl ether
t-butyl ethyl ether
t-amyl methyl ether
Propyl ether
Butyl ethyl ether
Amyl methyl ether
Isobutyl ether
Butyl ether
Cyclic Ethers Tetrahydrofuran
2-methyl tetrahydrofuran
Tetrahydropyran
Dimethyl tetrahydrofuran
2,2-dimethyl-1,4-dioxolane
1,4-Dioxane
1,3-Dioxane
3-methyl tetrahydropyran
4-methyl-1,3-dioxolane
1,3-Dioxepane
Methyl tetrahydrofurfuryl ether

TABLE 1-continued

Suitable Solvents

Non-cyclic Esters

Ethyl acetate
Methyl isobutyrate
t-butyl acetate
Methyl butyrate
Propyl acetate
Ethyl isobutyrate
s-butyl acetate
Methyl isovalerate
Isobutyl acetate
t-butyl propionate
Ethyl butyrate
Propyl propionate
Butyl acetate
Isoamyl acetate
Butyl propionate Ketones are preferred solvents with materials such as methyl ethyl ketone (MFK), methyl isobutyl ketone (MIBK) and methyl isopropyl ketone (MIPK) being most preferred.

The solution of the alkylamine in the organic solvent is generally made as concentrated in amine as possible. It can, however, range in concentration from about 1% by weight to saturation, which is about 25%–50% by weight in the case of the more soluble of these amines, such as TMA. The organic solution of alkylamine can contain other materials added to improve or facilitate processing. These can include antifoam agents, corrosion inhibitors, and the like, as will be known to those of skill in the art. The amine concentration can be increased by dissolving under pressure of up to about 5 atmospheres as well. The organic solvent is the principal solvent for the alkylamines. Only minor amounts of water are typically present, such as less than 10% by weight, preferably less than 3% by weight and more preferably less than 1% by weight.

Solid Sorbent Materials

The organic solution of alkylamine is used to resolubilize carboxylic acid adsorbed onto a solid or gel adsorbent. In addition to basic, polymeric solid sorbents, these solid phase materials include high surface area, relatively inert materials such as carbon black, or the like. Representative carbon black adsorbents are listed in Table 2.

TABLE 2

Activated Carbon Solid Adsorbents

| Carbon | Source |
| --- | --- |
| G-BAC | Union Carbide |
| Row 0.8S | Norit |
| Filtrasorb | |
| 100 | Calgon |
| 200 | Calgon |
| 300 | Calgon |
| 400 | Calgon |
| SE-340 | Rohm & Haas |
| SE-348 | Rohm & Haas |

They also include basic ion exchange resins such as pyridyl, pyridinium and amine group-containing resins. While defined as "ion exchange" resins, it will be appreciated that in many cases these materials are used for their basicity (amine functionality) and not for their ionic exchange potential. These materials include resins with these groups as part of their backbone structure as well as materials which have these groups appended from their backbones. These resin materials are available commercially as basic ion exchange resins. Representative resins are listed in Table 3.

TABLE 3

Ion Exchange Solid Adsorbents

| Commercial Designation | Source | Type of Adsorbent |
|---|---|---|
| AMBERLITE | | |
| XAD-7 | Rohm & Haas Corp. | Acrylic ester-Divinylbenzene |
| XAD-12 | Rohm & Haas Corp. | Poly(N-oxide) |
| XE-309 | Rohm & Haas Corp. | Poly(4-Vinylpyridine) |
| IRA-35 | Rohm & Haas Corp. | Acrylic-Divinylbenzene with Tertiary-Amine Groups |
| XE-378 | Rohm & Haas Corp. | Poly(2-Vinylpyridine) |
| DOWEX | | |
| WGR | Dow Chemical Company | Epoxy Polymer with Tertiary-Amine Groups |
| MWA-1 | Dow Chemical Company | Styrene-Divinylbenzene Copolymer with Primarily Tertiary-Araine Groups and ~ 10% Quarternary-Amine Groups |
| A-340 | Diamond Shamrock, Inc. | (Duolite) Polyethylene-Diamine, Cross-linked with Epichlorohydrin (a-gel-type resin) |
| AG3-X4 | Bio-Rad | Epoxy-amine Polymer with Primarily Tertiary Amine Groups and ~ 10% Quaternary Groups |
| REILLEX | | |
| 425 | Reilly Tar & Chemical Co. | Poly(4-Vinylpyridine) |
| 402 | | |

The Acids Recovered

The acids liberated and recovered in the regeneration process of the invention are carboxylic acids. These acids include aliphatic carboxylic acids of 2–20 carbons and aromatic carboxylic acids of 7–20 carbons. The aliphatic carboxylic acids include 2–20 carbon monoacids such as acetic acid, propionic acid, butyric acid, pentanoic acid, hexanoic acid, octanoic acid, dodecanoic acid and the like. The process is especially effective with polycarboxylic acids such as the di-, tri- and higher carboxyl materials, including the commonly known even-carbon-numbered diacids of 2–12 carbons (that is, the better known dicarboxylic acids of 2, 4, 6, 8, 10 or 12 carbon atoms, such as oxalic acid, succinic acid, sebacic acid, adipic acid and fumaric acid). Of course, the process also works with the odd-numbered acids, as well. Lactic acid, malic acid and citric acid are representative hydroxy-containing acids which can be recovered by this process.

The aromatic acids include aromatic monoacids of 7–13 carbons such as benzoic acid, cinnamic acid, phenylacetic acid, naphthoic acid, and the like, and diacids of 8–12 carbons such as phthalic acid. In addition to the simple oxyhydrocarbon acids, the process can, under appropriate conditions, be used to recover those more complex materials such as amino acids, and the like, which are of value and which often occur in aqueous solutions and need to be recovered therefrom.

Functional groups such as halogens or nitro groups may be present in the carboxylic acids recovered by the process of this invention.

When these acids are initially present in and recovered from water-based feedstocks in an overall sorption-regeneration process, the feedstocks will contain from about ten parts per million to saturation (e.g., up to about 40% by weight) and especially from 0.1% to 25% by weight of recoverable carboxylic acids. The feedstocks can contain a mixture of these acids, in which case the present process can either recover all of the acids or, if differences in forward sorption or back-desorption with the alkylamine permit, can fractionate the acid mixture. The present invention finds application with prepared feedstocks such as fermentation broths and the like; it also finds application with contaminated aqueous streams. Accordingly, the feedstocks can contain other materials such as salts and organics (e.g., sugars, starches, alcohols, aldehydes and the like). Typically, however, these other materials do not substantially follow the carboxylic acids as they are sorbed and resolubilized. Thus, they do not significantly interfere with the process of this invention. Materials that do interfere with this process include mineral acids or bases (e.g., HCl, $H_2SO_4$ and NaOH).

As noted, these acid materials removed and recovered by the process range in size from about 2 carbons (acetic acid) to about 20 carbons and can include monocarboxylic acids, di- and polycarboxylic acids, hydroxycarboxylic acids, and the like. The acid can be aliphatic or aromatic. This wide range of materials spans a range of physical forms. A few of these acids, for example, the 2 to 4 carbon monocarboxylic acids, are relatively volatile liquids.

| | |
|---|---|
| $C_2$— Acetic Acid | 118° C. b.p. |
| $C_3$— Propionic Acid | 141° C. b.p. |
| $C_4$— Butyric Acid | 165° C. b.p. |

Lactic acid is hard to crystallize and usually exists as a concentrated viscous solution. Many of the rest of these acids, especially the dicarboxylic acids, exist as insoluble solids at room temperature. The physical form of the free acids can play a part in the selection of the alkylamine and the solvent employed in the regeneration.

As noted previously, in the amine/carboxylic acid complex decomposition steps of the regeneration process, a forward driving force is needed to assure substantial conversion of the complex. This driving force typically is provided by separating the free amine from the free acid and removing one or both products from the reaction zone. Preferential vaporization of one product from the other is very convenient and a preferred way to carry out this separation.

This invention will be further illustrated by the following Examples.

EXAMPLE 1

Materials

All aqueous solutions were prepared from distilled water which had been passed through a Milli-Q water purification system (Millipore Corp.). Lactic acid (Aldrich, 85+% in water) was diluted with water to approximately 15 wt % and boiled under constant reflux for at least 12 hours to hydrolyze any lactic acid polymers.

The polymeric sorbent utilized was Dowex MWA-1 (Dow Chemical Co.). This sorbent is macroreticular and contains tertiary amine functionalities, with up to 10% of the total amine functionality in the quarternary ammonium form. Prior to use, it was washed repeatedly and dried to constant weight in a vacuum oven (VWR Scientific, Inc., Model 1410D). The activated carbon, Westvaco WV-B was used as received.

The regenerant solution was prepared by bubbling gaseous trimethylamine (TMA, Matheson, anhydrous) in methyl ethyl ketone (MEK, Fisher Scientific) or methyl isobutyl ketone (MiBK, Sigma-Aldrich). Typical organic-phase water concentrations were <5×10$^{-4}$ g H$_2$O/g solution. Water concentrations were measured by Karl Fisher titration using a methanol-free, ketone-compatible solvent (GFS Chemicals).

Methods-Sorbent Leaching

To prepare lactic-acid-laden sorbent for regeneration, known weights of sorbent (typically 0.5 g) and acid solution (typically 5.0 g) were contacted in 20-mL scintillation vials sealed with TEFLON-lined caps. The vials were placed in a constant-temperature shaker bath (Fisher Scientific, Versa-Bath® S) at 25° C. and 120 RPM for at least 24 hours. Previous studies with sorption of lactic acid on Dowex MWA-1 showed that equilibrium was reached within the experimental error in one hour (Tung and King). Aqueous-phase acid concentrations were determined by high-performance liquid chromatography (HPLC) using a Bio-Rad Aminex HPX-87H strong cation-exchange column, a 0.01 N H$_2$SO$_4$ mobile phase, and an ultraviolet detector (Hewlett-Packard, Series 1050) operating at 210 nm.

Total solution uptakes were determined by weighing the sorbent samples following centrifugation in a 15-mL, coarse grade, fritted glass funnel enclosed within a plastic centrifuge tube. The centrifuge (Damon/IEC, Model HN-SII) was operated for 8 minutes at 2000 RPM. These conditions are sufficient to remove nearly all of the interstitial and adhering bulk liquid (Frierman, 1983).

To maintain an essentially anhydrous environment during regeneration, the sorbed water was removed from the "wet" acid-laden sorbent by drying to constant weight in a vacuum oven. The extremely low volatility of lactic acid ensured that losses of acid during this drying step were insignificant in comparison to the total acid uptake.

Regeneration isotherms were generated by contacting "dry" acid-laden sorbent with organic TMA solutions (0.3 to 14.3 wt. %) in 20-mL scintillation vials sealed with TEFLON-lined caps. The vials were placed in a constant-temperature shaker bath at 25° C. and 120 RPM for at least 24 hours. The solution to sorbent phase ratio for regeneration was generally 29–30 mL/g. The final leached sorbent was centrifuged and weighed as before to determine the total solution remaining in the pore volume.

To determine the remaining amount of sorbed acid following regeneration, the sorbent was leached with 1.0 N HCl solution to free any complexed lactic acid (with either the sorbent or TMA). The procedure for this leaching step is identical to that for regeneration. The solution to sorbent phase ratio for this leaching step was generally 10–11 mL/g. The lactic acid concentration in the final aqueous phase was determined by HPLC.

Methods-Thermal Cracking

Figure 2:
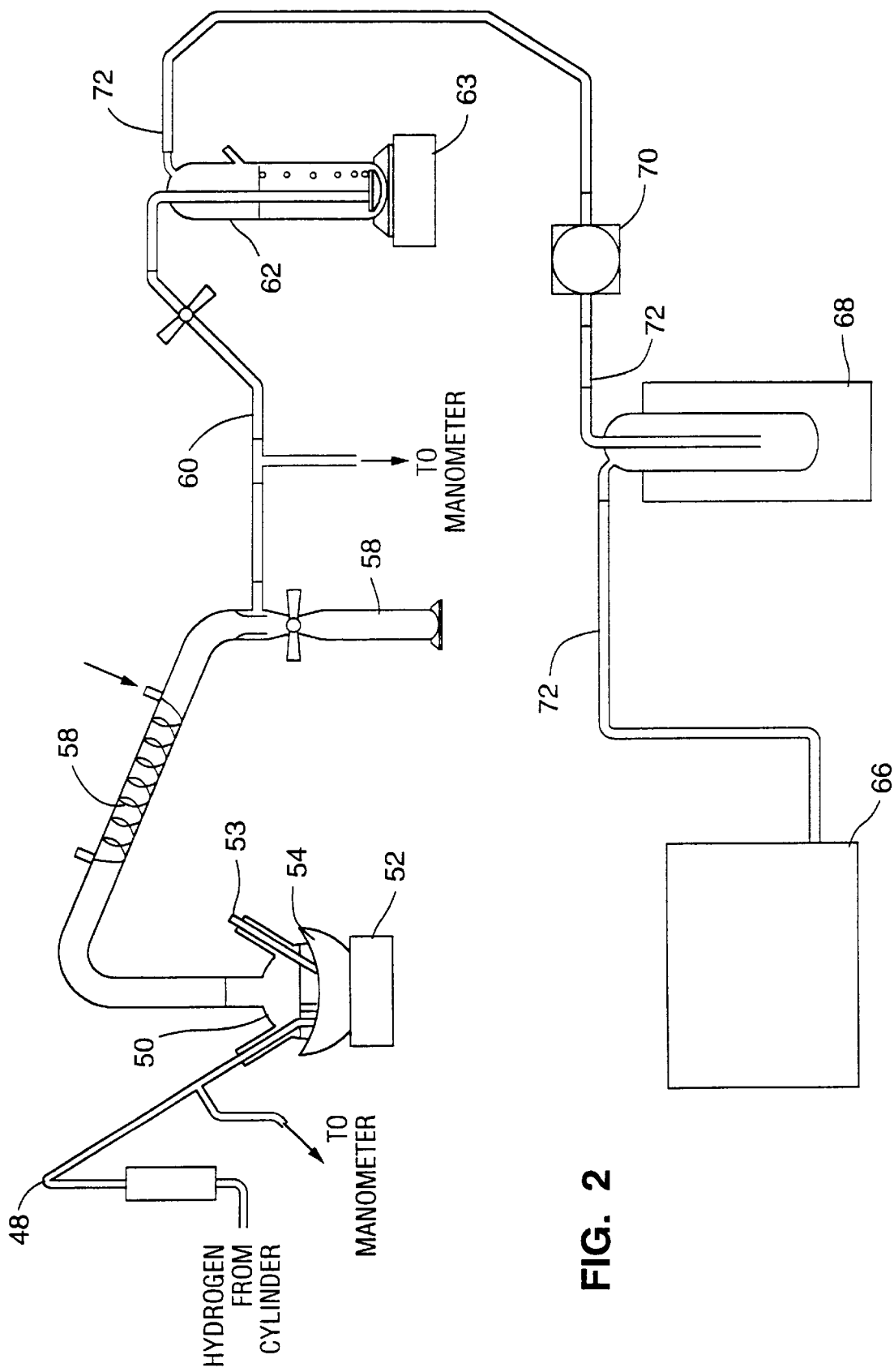
FIG. 2 is a schematic representation of an apparatus used in experiments to verify aspects of the process of this invention.

The apparatus used for thermal cracking of the TMA-lactic acid complex is depicted in FIG. 2. The organic solution was placed in a 3-neck, 100-mL, round-bottom flask 50 and equipped with a magnetic stir bar 52, thermometer 53, and a heating mantle 54. The solution was boiled under total reflux. The organic solvent taken overhead was condensed in condenser 56 and collected in collection cylinder 58. The TMA evolved was carried through line 60 to an absorber flask 62 containing dilute H$_2$SO$_4$ and agitated by a magnetic stirrer 63.

Nitrogen was bubbled through the TMA-lactic acid complex-containing solution via line 48. The decomposition was carried out at atmospheric pressure, but, if desired, a vacuum (to 350–380 mm Hg absolute) could be pulled on the reaction train via vacuum regulator 70, trap 68 and pump 66, all on line 72.

The temperature of the TMA-lactic acid complex solution was increased gradually from 25° C. to the solution boiling point of 80° C.

The rate of evolution of TMA was monitored by absorption into dilute H$_2$SO$_4$ containing methyl red as the indicator. At the beginning of a run, the absorber flask was filled with 500-mL of H$_2$SO$_4$ solution concentrated enough to neutralize 25% of the TMA initially present in the TMA-lactic acid solution. When 25% of the TMA had been absorbed, the solution changed color from red to yellow. At this point, the time was recorded and 5-mL of a concentrated solution of H$_2$SO$_4$ (enough to neutralize another 10% of the TMA) was injected into the absorber flask. This process was repeated throughout the experiment. A sample of the final absorber solution was titrated with 0.0794 N NaOH to determine the amount of TMA that had been absorbed between the last color change and the end of the experimental run. The amount of TMA remaining in the initial TMA-lactic acid solution was determined by HPLC using a Bio-Rad Aminex HPX-72-0 organic-base-analysis column, a 0.01 N NaOH mobile phase, and an ultraviolet detector (Hewlett-Packard, Series 1050) operating at 214 nm.

Product Purification

Treatment of the final acid solution with activated carbon was examined as a purification technique to remove colored impurities. A sample of the final TMA-lactic acid solution was diluted in water and contacted with a known weight of Westvaco WV-B carbon for 1 minute. The solution was filtered to remove carbon fines. Changes in solution color were visually examined.

Results and Discussion

Sorbent Leaching

FIG. 3 shows the results for leaching lactic acid from Dowex MWA-1 with varying amounts of TMA in MEK solution. In this figure, percent regeneration refers to the percentage of the composite uptake of lactic acid recovered from the sorbent during regeneration. The composite uptake does not include lactic acid which was non-selectively sorbed. Approximately 78% recovery of lactic acid was achieved when 2 moles of TMA were present for every mole of acid adsorbed, and 90–91% recovery was obtained for 8–10 moles of TMA per mole of acid. The inability of the TMA to regenerate the basic sites of the sorbent fully probably reflects the quaternary ammonium content of the sorbent (Gustafson, et al., 1970).

Thermal Cracking

In the TMA-lactic acid thermal cracking experiments, essentially 100% of the total TMA initially present was recovered overhead. There was no odor of TMA left in the residual liquid. This result was confirmed by HPLC analysis of the final solution; TMA was absent in the chromatogram.

Figure 4:
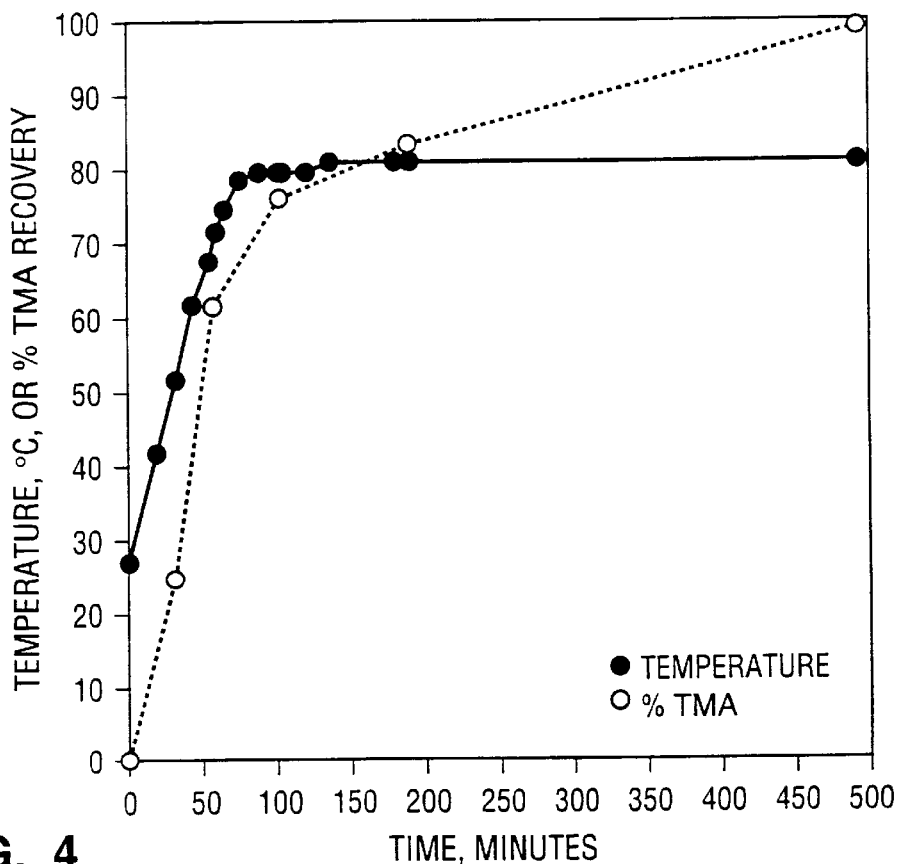
FIG. 4 is a time/temperature curve illustrating the rate of vaporization of trimethylamine during the decomposition of a trimethylamine/lactic acid complex in methyl ethyl ketone.

FIG. 4 presents the results of a typical thermal cracking experiment performed at atmospheric pressure under a nitrogen atmosphere. The rate of evolution of TMA is high during the initial stages of cracking, where the concentration of TMA is high. The rate decreases as the concentration of TMA in solution decreases. This result may be associated with a lower driving force for the cracking reaction at low concentrations of TMA.

The cracking temperature may also affect the rate of evolution of TMA. It may be possible to increase the cracking rate by increasing the cracking temperature. An increased cracking temperature could be achieved by operating at an elevated pressure or by selection of a higher boiling organic diluent. The overall cracking time could also be decreased by heating the solution at a higher rate initially.

Discoloration of the final solution was evident; the solution turned yellow upon heating at 80° C. Several possible causes of this discoloration exist, however, the most likely source of color is a caramelization reaction involving lactic acid and/or trace amounts of sugar and/or TMA. Discoloration of lactic acid upon heating is common, and usually occurs in the presence of residual sugars (Vickroy, 1985). Thus, the discoloration observed in the final solution may be due to interactions between trace amounts of residual sugars present in the original lactic acid and/or TMA and/or lactic acid.

Treatment of the final acid solution with activated carbon was effective at eliminating colored impurities; the final solution was colorless following this treatment. In a commercial process it is desirable for a carbon adsorbent used for decolorization to exhibit low capacity for lactic acid. Several investigators have measured uptake capacities for lactic acid on activated carbon (e.g., Bartell and Miller, 1923; Linner and Gortner, 1935). The capacities range from 0.72–1.01 mmol/g for the carbons studied. However, these studies did not address the effect of carbon type on acid uptake. Exploiting surface chemistry properties of carbons from different sources and activated or treated by different methods may result in acid uptakes much lower than those previously recorded (Kilduff and King, 1996).

Conclusions

Lactic-acid-laden Dowex MWA-1 is 90% regenerated by leaching with an organic solution of TMA. The inability of the TMA to fully regenerate the sorbent is a consequence of its inability to regenerate strongly-basic, quaternary ammonium sites. Upon repeated reuse, the sorbent should sustain about 90% of its initial capacity, an acceptable figure.

The resulting TMA-lactic acid complex can be cracked thermally to yield acid product and TMA, available for recycle. The cracking reaction is essentially 100% complete when regeneration is performed by leaching with an organic solution of TMA.

Colored impurities in the final acid product are removed by treatment with activated carbon.

EXAMPLE 2

The experiments set forth in Example 1 are repeated twice replacing the aqueous solution of lactic acid starting material with a similar concentration aqueous solutions of fumaric acid and succinic acid. The same resin and MEK-TMA regeneration solution used in Example 1 are employed. Similar results and similarly complete decomposition of the resulting trimethylamine/fumaric acid complex and trimethylamine/succinic acid complex as observed with the complex in Example 1 would be achieved.

EXAMPLE 3

The experiments set forth in Example 1 are repeated replacing the Dowex MWA-1 resin with a similar amount of Bio-Rad AG3-X4 resin. The same aqueous acid solution and MEK-TMA regeneration solution used in Example 1 are employed. Similar results and similarly complete regeneration of the resin and recovery of the resulting free acid and amine as observed in Example 1 would be achieved.

EXAMPLE 4

Figure 5:
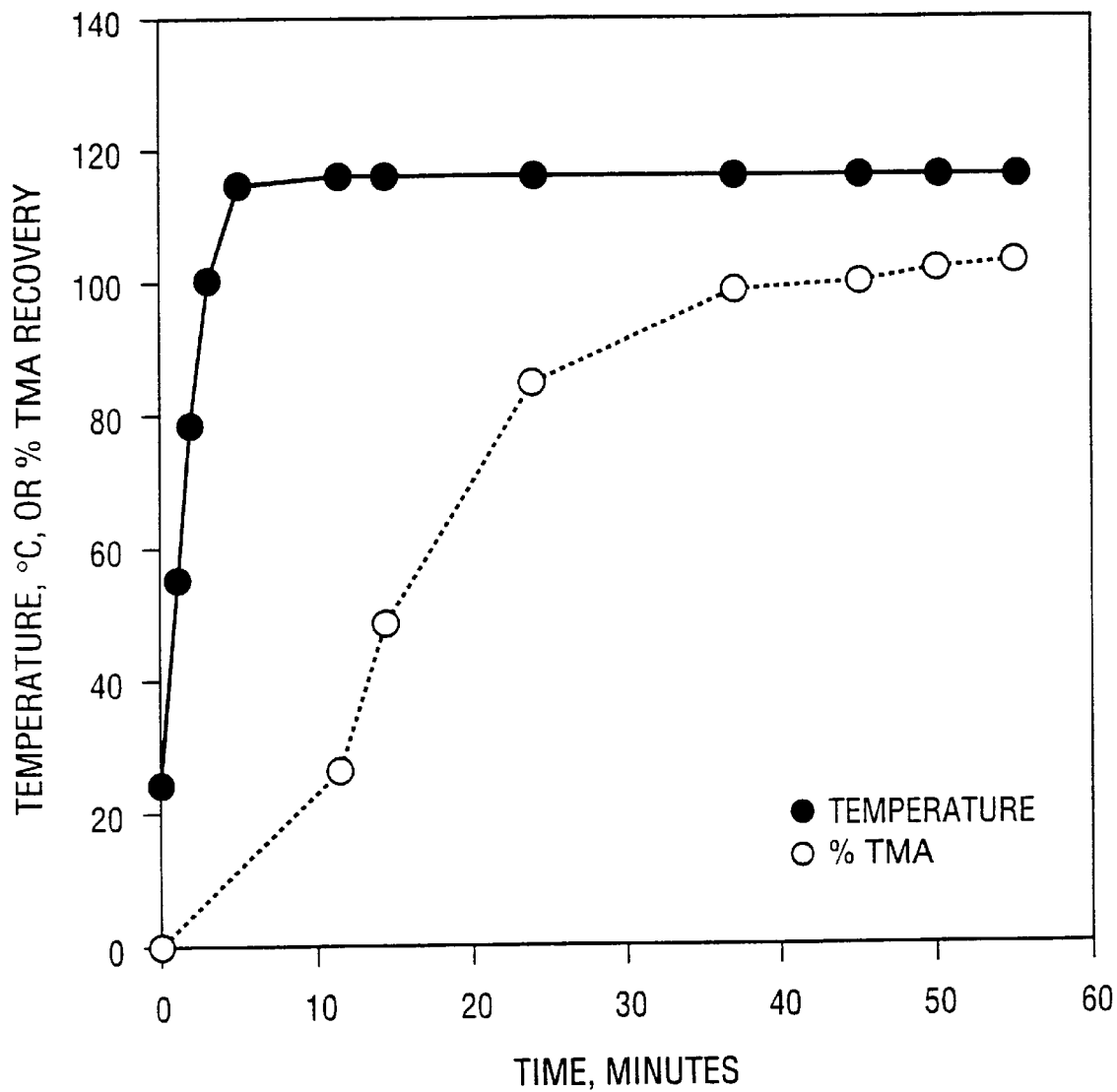
FIG. 5 is a time/temperature curve illustrating the rate of vaporization of trimethylamine during the decomposition of trimethylamine/lactic acid complex in methyl isobutyl ketone.

The experiment set forth in Example 1 was repeated replacing the MEK organic solvent with methyl isobutyl ketone (MIBK). The same resin and TMA used in Example 1 was employed. Similar results were achieved, albeit at a higher cracking temperature and a much shorter cracking residence time. FIG. 5 presents the results of the thermal cracking.

EXAMPLE 5

The experiments set forth in Example 1 are repeated three times replacing the MEK organic solvent with methyl isopropyl ketone, isopropyl ether, and propyl acetate, respectively. The same resin and TMA used in Example 1 are employed. Similar results and similarly complete decomposition of the resulting trimethylamine/lactic acid complex as observed in Example 1 would be achieved.

EXAMPLE 6

The experiments set forth in Example 1 are repeated replacing the TMA with triethylamine. The same resin used in Example 1 is employed. Similar results and similarly complete decomposition of the resulting triethylamine/lactic acid complex as observed in Example 1 would be achieved.

EXAMPLE 7

Materials

Aqueous solutions of sodium lactate were prepared by combining equal moles of sodium hydroxide and lactic acid. The polymeric sorbent utilized was Dowex MWA-1 (Dow Chemical Co.) Carbon dioxide ($CO_2$) was obtained from The BOC Group, Inc.

Methods

Known weights of sorbent (typically 5 g) and sodium lactate solution (typically 50 g) were contacted in a 125-mL glass vial sealed with 3-mm thick silicone septa. The vial was placed in a constant-temperature bath maintained at 25° C. The solution was stirred continuously with a magnetic stir bar. To purge the system of air, $CO_2$ was introduced to the vial through a syringe connected to a pressurized $CO_2$ gas cylinder. Air and $CO_2$ exited the vial through a second syringe connected to a bubble flow meter to measure the flow rate of $CO_2$ into the vial. When the system had been purged of air, the syringe connected to the bubble flow meter was removed from the vial, and the system was pressurized with $CO_2$ to the desired working pressure (1.0–3.2 bar). The syringe connected to the $CO_2$ cylinder was left in place to assure the pressure did not change in the event of any system leaks. After 24 hours, the concentration of lactate in the solution was measured to calculate the amount of lactate anion removed by adsorption of lactic acid onto the sorbent. Unpublished results of sorption of lactic acid on Dowex MWA-1 in the presence of $CO_2$ showed that equilibrium was reached within the experimental error in 3 hours. Aqueous-phase acid concentrations were determined by high-performance liquid chromatography (HPLC).

Results and Discussion

FIG. 7 shows the equilibrium uptake isotherm for $CO_2$-aided adsorption of lactic acid onto Dowex MWA-1 at 25° C. from a 0.05 M solution of sodium lactate. Experimental data are represented by symbols. The line represents a mathematical model to describe adsorption equilibria for this system. The model includes chemical equilibria, mass and charge-balance equations that describe the system. The model uses no fitting parameters. All input parameters were obtained from independent measurements. An equilibrium constant for adsorption of carbonic acid on Dowex MWA-1, $K_c$, was estimated from a linear free-energy relation (LFER) correlating $\ln(K)$ with $DpK_a \equiv pK_{a,sorbent} - pK_{a,acid}$. This LFER was developed from data for adsorption of lactic acid on various sorbents (Tung and King, 1994). The open circle at P=0 represents the uptake of lactate anion from a 0.05 M sodium lactate solution in the absence of $CO_2$. The model prediction is in close agreement with the experimental data. The uptake value at 3.2 bar corresponds to a 65.5% recovery of lactate anion from the initial solution. This value is 3 times higher than the 21.6% recovery in the absence of $CO_2$.

What is claimed is:

1. A process for recovering carboxylic acid from a carboxylic acid-containing aqueous feed stream comprising:

(a) contacting the carboxylic acid-containing feed stream with a solid phase acid sorbent under conditions whereby carboxylic acid is sorbed from the feed stream to the solid phase acid sorbent, thereby forming an acid-depleted aqueous feed stream and an acid-enriched solid phase acid sorbent;

(b) separating the acid-depleted aqueous feed stream from the acid-enriched solid phase acid sorbent;

(c) contacting the separated acid-enriched solid phase acid sorbent with a desorbing solution comprising an alkylamine in an organic solvent, thereby solubilizing the carboxylic acid from the sorbing phase into the desorbing solution as an alkylamine/carboxylic acid complex, and forming a carboxylic acid-lean solid phase acid sorbent;

(d) separating the alkylamine/carboxylic acid complex-containing desorbing solution from the carboxylic acid-lean solid phase acid sorbent;

(e) treating the alkylamine/carboxylic acid complex-containing desorbing solution to decompose the alkylamine/carboxylic acid complex to yield the carboxylic acid and the alkylamine; and (f) separating the alkylamine and the carboxylic acid and (g) recovering the carboxylic acid and the alkylamine separated in step (f).

2. The process of claim 1 wherein the treating of step (e) comprises heating.

3. The process of claim 2 wherein the organic solvent is an organic liquid which does not react with the acid or the alkylamine, is easily removed from the solid sorbent under conditions which do not degrade the sorbent, is volatile enough to be easily removed from the acid, has a high solubility for the alkylamine, and has a boiling point high enough for the decomposing to occur at a reasonable rate and low enough to prevent side reactions.

4. The process of claim 3 wherein the organic solvent is selected from the group consisting of aldehydes, ethers, esters and ketones having from 3 to 7 carbon atoms.

5. The process of claim 4 wherein the alkylamine is a trialkylamine.

6. The process of claim 4 wherein the alkylamine is trimethylamine.

7. The process of claim 6 wherein the organic solvent is a ketone.

8. the process of claim 7 wherein the ketone is methyl isobutyl ketone.

9. the process of claim 7 wherein the ketone is methyl ethyl ketone.

10. the process of claim 7 wherein the carboxylic acid is lactic acid.

11. A process for regenerating a carboxylic acid-enriched solid phase acid sorb comprising:

(a) contacting the acid-enriched solid phase acid sorbent with a desorbing solution comprising an alkylamine in an organic solvent, thereby solubilizing the carboxylic acid from the sorbing phase into the desorbing solution as an alkylamine/carboxylic acid complex, and forming a carboxylic acid-lean solid phase acid sorbent;

(b) separating the alkylamine/carboxylic acid complex-containing desorbing solution from the carboxylic acid-lean solid phase acid sorbent;

(c) treating the alkylamine/carboxylic acid complex-containing desorbing solution to decompose the alkylamine/carboxylic acid complex to yield the carboxylic acid and the alkylamine; and (d) separating the alkylamine and the carboxylic acid and (e) recovering the carboxylic acid and the alkylamine separated in step (d).

12. The process of claim 11 wherein the treating of step (c) comprises heating.

13. The process of claim 12 wherein the organic solvent is an organic liquid which does not react with the acid or the alkylamine, is easily removed from the solid sorbent under conditions which do not degrade the sorbent, is volatile enough to be easily removed from the acid, has a high solubility for the alkylamine, and has a boiling point high enough for the decomposing to occur at a reasonable rate and low enough to prevent side reactions.

14. The process of claim 13 wherein the organic solvent is selected from the group consisting of aldehydes, ethers, esters and ketones having from 3 to 7 carbon atoms.

15. The process of claim 14 wherein the alkylamine is a trialkylamine.

16. The process of claim 15 wherein the alkylamine is trimethylamine.

17. The process of claim 16 wherein the organic solvent is a ketone.

18. The process of claim 17 wherein the ketone is methyl isobutyl ketone.

19. The process of claim 17 wherein the ketone is methyl ethyl ketone.

20. The process of claim 17 wherein the carboxylic acid is lactic acid.

21. A process for recovering carboxylic acid from a carboxylic acid-containing aqueous feed stream comprising:

(a) contacting the carboxylic acid-containing feed stream with a solid phase acid sorbent in the presence of a positive pressure of added carbon dioxide under conditions whereby carboxylic acid is sorbed from the feed stream to the solid phase acid sorbent and carbon dioxide is converted into carbonate and/or bicarbonate, thereby forming an acid-depleted, carbonate and/or bicarbonate-containing aqueous feed stream and an acid-enriched solid phase acid sorbent;

(b) separating the acid-depleted, carbonate and/or bicarbonate-containing aqueous feed stream from the acid-enriched solid phase acid sorbent;

(c) contacting the separated acid-enriched solid phase acid sorbent with a desorbing solution comprising an alkylamine in an organic solvent, thereby solubilizing the carboxylic acid from the sorbing phase into the desorbing solution as an alkylamine/carboxylic acid complex, and forming a carboxylic acid-lean solid phase acid sorbent;

(d) separating the alkylamine/carboxylic acid complex-containing desorbing solution from the carboxylic acid-lean solid phase acid sorbent;

(e) treating the alkylamine/carboxylic acid complex-containing desorbing solution to decompose the alkylamine/carboxylic acid complex to yield the carboxylic acid and the alkylamine; and (f) separating the alkylamine and the carboxylic acid and (g) recovering the carboxylic acid and the alkylamine separated in step (f).

22. The process of claim 21 wherein the treating of step (e) comprises heating.

23. The process of claim 22 wherein the organic solvent is selected from the group consisting of aldehydes, ethers, esters and ketones having from 3 to 7 carbon atoms.

24. The process of claim 23 wherein the alkylamine is a trialkylamine.

25. The process of claim 24 wherein the alkylamine is trimethylamine.

26. The process of claim 25 wherein the organic solvent is a ketone.

27. The process of claim 26 wherein the ketone is methyl isobutyl ketone.

28. The process of claim 27 wherein the ketone is methyl ethyl ketone.

29. The process of claim 28 wherein the carboxylic acid is lactic acid.

30. A process for recovering carboxylic acid from a carboxylic acid-containing aqueous feed stream comprising:
- (a) contacting the carboxylic acid-containing feed stream with a solid phase acid sorbent in the presence of a positive pressure of added carbon dioxide under conditions whereby carboxylic acid is sorbed from the feed stream to the solid phase acid sorbent and carbon dioxide is converted into carbonate and/or bicarbonate, thereby forming an acid-depleted, carbonate and/or bicarbonate-containing aqueous feed stream and an acid-enriched solid phase acid sorbent;
- (b) separating the acid-depleted, carbonate and/or bicarbonate-containing aqueous feed stream from the acid-enriched solid phase acid sorbent;
- (c) treating the acid-depleted, carbonate and/or bicarbonate-containing aqueous feed stream to convert carbonate and/or bicarbonate to carbon dioxide for recycle to step (a);
- (d) contacting the separated acid-enriched solid phase acid sorbent with a desorbing solution comprising an alkylamine in an organic solvent, thereby solubilizing the carboxylic acid from the sorbing phase into the desorbing solution as an alkylamine/carboxylic acid complex, and forming a carboxylic acid-lean solid phase acid sorbent;
- (e) separating the alkylamine/carboxylic acid complex-containing desorbing solution from the carboxylic acid-lean solid phase acid sorbent;
- (f) treating the alkylamine/carboxylic acid complex-containing desorbing solution to decompose the alkylamine/carboxylic acid complex to yield the carboxylic acid and the alkylamine; and
- (g) separating the alkylamine and the carboxylic acid and
- (h) recovering the carboxylic acid and the alkylamine separated in step (g).

31. A process for recovering carboxylic acid from a carboxylic acid-containing aqueous feed stream comprising:
- (a) contacting the carboxylic acid-containing feed stream with a solid phase acid sorbent in the presence of a positive pressure of added carbon dioxide under conditions whereby carboxylic acid is sorbed from the feed stream to the solid phase acid sorbent and carbon dioxide is converted into carbonate and/or bicarbonate, thereby forming an acid-depleted, carbonate and/or bicarbonate-containing aqueous feed stream and an acid-enriched solid phase acid sorbent;
- (b) separating the acid-depleted, carbonate and/or bicarbonate-containing aqueous feed stream from the acid-enriched solid phase acid sorbent;
- (c) subjecting the separated acid-enriched solid phase acid sorbent to desorption conditions, thereby desorbing the carboxylic acid from the sorbing phase and forming a carboxylic acid-lean solid phase acid sorbent;
- (d) separating the desorbed carboxylic acid from the carboxylic acid-lean solid phase acid sorbent, and
- (e) recovering the desorbed carboxylic acid separated in step (d).

32. The process of claim 31 additionally comprising the step of
- (f) treating the carbonate and/or bicarbonate-containing aqueous feed stream to convert carbonate and/or bicarbonate to carbon dioxide for recycle to step (a);

wherein the alkylamine is trimethylamine.

33. The process of claim 31 wherein the solid phase sorbent is a basic solid phase sorbent.

34. The process of claim 31 wherein said desorption conditions comprise contact with a desorbing solution.

* * * * *